United States Patent [19]

Baldwin

[11] 4,408,996
[45] Oct. 11, 1983

[54] PROCESS FOR DYEING ABSORBENT MICROBIOCIDAL FABRIC AND PRODUCT SO PRODUCED

[75] Inventor: A. Frank Baldwin, Greensboro, N.C.

[73] Assignee: Burlington Industries, Inc., Greensboro, N.C.

[21] Appl. No.: 310,416

[22] Filed: Oct. 9, 1981

[51] Int. Cl.$^3$ .................. D06P 5/02; A01N 1/02; B05D 3/02; A61F 13/00

[52] U.S. Cl. .................. 8/490; 128/132 D; 424/16; 424/184; 427/2; 427/387; 427/389; 427/389.9; 427/391; 427/393.4; 604/358; 604/375

[58] Field of Search ............ 8/490; 427/2, 387, 389.9, 427/393.4, 391, 389; 424/16, 184; 128/132 D, 290 R, 290 P, 290 W

[56] References Cited

U.S. PATENT DOCUMENTS

| | | | |
|---|---|---|---|
| 3,247,280 | 4/1966 | Kanner | 260/824 |
| 3,488,217 | 1/1970 | Ryan et al. | 427/386 |
| 3,560,442 | 2/1971 | Golitz et al. | 427/387 X |
| 3,660,008 | 5/1972 | Kissa | 8/21 A |
| 3,730,701 | 5/1973 | Isquith et al. | 71/67 |
| 3,788,803 | 1/1974 | Klein et al. | 8/17 |
| 3,794,736 | 2/1974 | Abbott et al. | 424/78 |
| 3,796,686 | 3/1974 | Golitz et al. | 427/387 X |
| 3,817,739 | 6/1974 | Abbott et al. | 71/67 |
| 4,035,411 | 7/1977 | Heckert et al. | 428/543 X |
| 4184004 | 1/1980 | Pines et al. | 428/413 |
| 4,262,043 | 4/1981 | Wald | 427/387 |

Primary Examiner—Norman Morgenstern
Assistant Examiner—Thurman K. Page
Attorney, Agent, or Firm—Cushman, Darby & Cushman

[57] ABSTRACT

Dyed, absorbent bioactive wettable fabrics are prepared by mixing together a wettable hydrophilic organosilicone polymer, a tinctorial amount of a compatible direct dye and a bioactive silyl quanternary amine. The mixture is applied to a non-woven cellulose-containing substrate then heated to dye the coated substrate, fix the dye and couple the microbiocide and hydrophilic coupling agent to the substrate. Fabric so produced is useful as an absorbent surgical drape or dressing to isolate a surgical incision site while providing an absorbent antimicrobial field to destroy migrating and cross-contaminating bacteria, algae and fungi.

6 Claims, 1 Drawing Figure

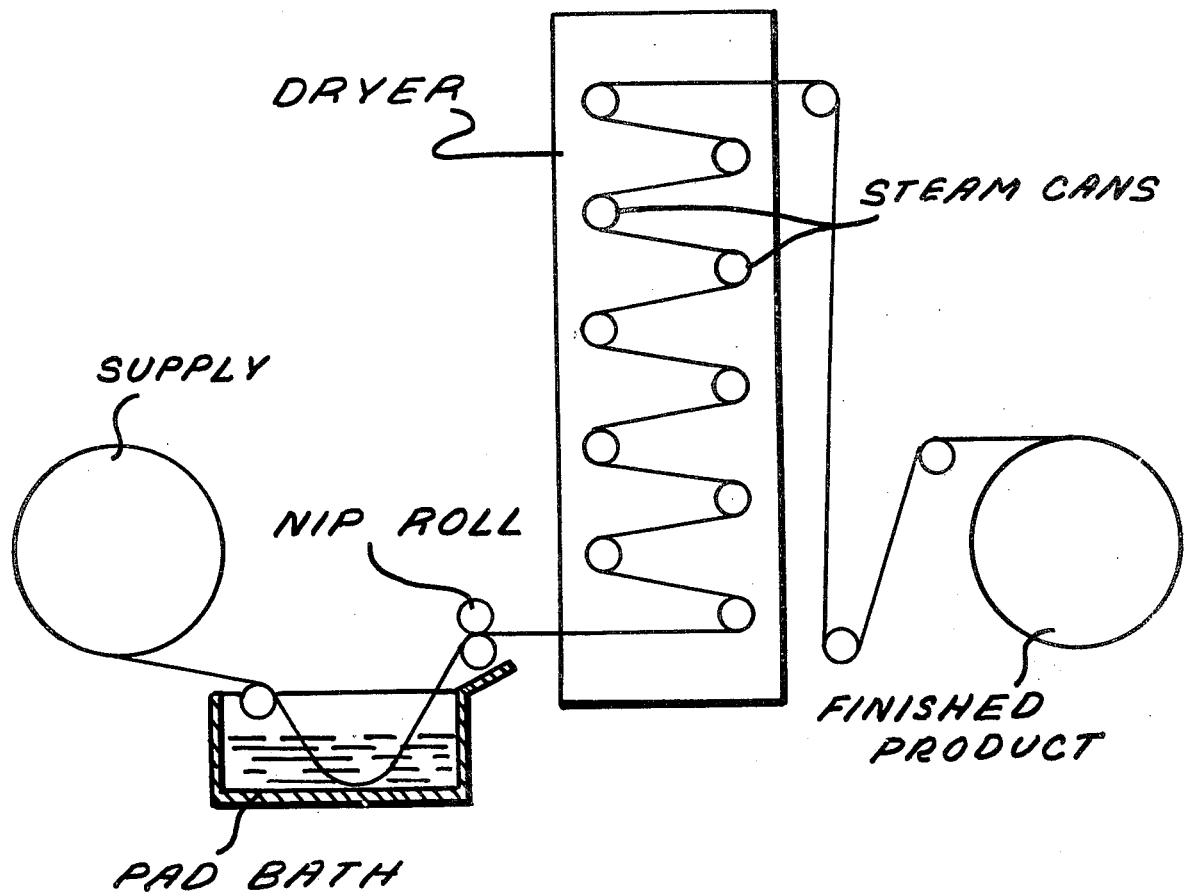

PROCESS FOR DYEING ABSORBENT MICROBIOCIDAL FABRIC AND PRODUCT SO PRODUCED

This invention relates to a process for dyeing absorbent fabric suitable for use as a surgical drape, dressing or the like which is used to isolate a surgical incision site and at the same time provides an absorbent antimicrobial field which becomes substantive on the fabric and services to destroy migrating and cross-contaminating bacteria, fungi and algae. Such fabric is colored, highly wettable, bioactive and serves to lower the amount of microbial contamination while lowering the risk of post-operative infection.

BACKGROUND OF THE INVENTION

A need exists for a dyed surgical drape, bandage or like product that kills bacteria but is itself non-toxic, that provides permanent antimicrobial capacity yet the antimicrobial agent itself is not extracted from the fabric in use and that maintains its effectiveness over a period of time but is not inhibited by sterilization, storage or handling.

A particularly useful antimicrobial agent is Q9–5700, an antimicrobial agent available from Dow Corning Corporation of Midland, Mich. The material is a silicone quaternary amine, chemically 3-(trimethoxysilyl)-propyloctadecyl dimethyl ammonium chloride. This material has been used to protect textiles and inhibit odor-causing bacteria and fungi which contamination may result in odor problems, discoloration and deterioration of these textiles. Application of this type of silicone quaternary amine onto the surface of textiles has been found to inhibit the growth of microorganisms and to aid in the control of the above-mentioned problems. As such it is authorized by the Environmental Protection Agency of the United States Government for use on textile surfaces (EPA No. 34292-1) and it has also been accepted by the Food and Drug Administration of the U.S. Government for use in medical devices for use association with humans and animals.

Surgical drapes and like materials are typically made of non-woven textiles or other non-woven type materials, however when such silicone quaternary amines are applied to a non-woven substrate it was found that the substrate was rendered hydrophobic, thus aqueous-based fluids, including normal body fluids, were repelled by such a coated substrate. Further difficulties were encountered in maintaining the integrity of the silicone quaternary amine in or on the substrate and preventing it from leaching away from the substrate and possibly contaminating patients's surface area surrounding the site of the surgical procedure and even possibly contaminating the surgical opening itself.

The requirements for a successful medical fabric or substrate include the following:

1. The substrate must be bioactive, that is it much achieve a 95% or better bactericidal effect within one hour. In other words, the material is bacteriocidal and not merely bacteriostatic as is the case with the wearing apparel.
2. The bioactive/bactericidal material must remain on the substrate and not be leached from the substrate, but if leaching occurs it must be virtually undetectable, i.e. only less than 70 parts per billion (70 ppb) from a 6 inch × 6 inch swatch according to test procedures, described in more detail below. Non-leachability or substantial non-leachability is a factor of the fabric sample or swatch size being tested.
3. The leachate removed from a sample of the medical substrate must not exhibit cytotoxicity to cells. This includes not only the antimicrobial agent itself but also other finishes, colorants or the like that may also be applied to the substrate. A typical testing procedure includes adding a standardized cell culture to a leachate recovered from a predetermined sample size of the substrate being tested, incubating the culture plus leachate and observing the culture for either cell death or morphological change to the cells in the culture.
4. The medical substrate must be nonflammable in accordance with standard CS-191-53.
5. The medical substrate must conform to the antistatic requirements of test NFPA 56-A.
6. The substrate itself must be absorptive of normal body fluids, such as physiological saline, and blood.
7. The dye must stay on the substrate and be fixed thereto thus free from crocking and water bleeding.

In addition to providing a medical substrate that satisfies all of the above-listed performance requirements it is also desirable from a commercial viewpoint, to color or dye the substrate an aesthetically pleasing color, for example blue or green, the colors of choice for equipment used in surgical procedures. Simply adding a tinctorial amount of the desired dye to a pad bath containing the bioactive compound does not provide the desired result—it appears that the strongly anionic nature of direct dyestuffs, commonly used to color paper and other cellulosic products, prevents the preparation of finishing baths containing both the strongly cationic bioactive compound and the anionic direct dyes. It is more efficient to apply the required finish, including color, to the cellulosic substrate in a single finishing step or bath than to use multiple baths, steps and drying operations.

It has been a continuing difficulty in the art to identify an appropriate finishing agent or group of agents that will inhibit the hydrophobicity imparted to the substrate by the silicone quaternary amine antimicrobial agent and provide a substrate conforming to the seven requirements identified above. Virtually all detergents commonly used as fabric softeners are leachable from a non-woven substrate and tend to lyse cells to at least some extent. For example, to be successfully used organic non-ionic surfactants may require a substantial amount of the surfactant on the substrate, for instance from 5 to 15%, calculated on the weight of the fabric.

Another difficulty encountered is in the selection of an appropriate substrate is that the silicone quaternary amine-type antimicrobial compounds do not readily adhere to polyester substrates and that as such the resulting product does not conform to the maximum leachability requirements, as stated above. Accordingly cellulosic substrates are preferred, although minor amounts of polyester in a cellulosic/polyester blend may be tolerated.

Suitable finishing agents, antimicrobial agents and operational parameters are disclosed in my copending application Ser. No. 310,414 filed on even date herewith, the disclosure of which is hereby incorporated by reference.

BRIEF DESCRIPTION OF THE FIGURE

The attached drawing schematically represents the process of my invention.

DETAILED DESCRIPTION OF THE INVENTION

I have found, and hereby disclose, a process for preparing a dyed, absorptive, bacteriostatic non-woven medical substrate in which a solution of a specific silicone quaternary amine is applied with a direct dye and a member of a specific class of rewetting agents which act as hydrophilic coupling agents to secure the quaternary amine+rewetting agent+direct dye to the substrate. The rewetting agent improves the compatibility of anionic direct dye with the cationic quaternary amine antimicrobial agent and imparts the necessary water absorptive qualities in the product yet become substantive (non-leachable) on the fabric meeting the bioactivity, leachability, cytotoxicity, non-flammability, antistatic and absorptive properties enumerated above.

According to the procedure of this invention a tinctorial amount of one or more direct dyes is slurried with an organosilicone terpolymer and to the resulting solution the desired amount of bioactive silyl quaternary amine is added. Typically the amounts of each of the three ingredients will be up to about 1 percent calculated on the dry weight of the fabric.

I have found that an aqueous-based solution preferably containing: (1) from about 0.2 to about 1.1% of 3-(trimethoxysilyl)-propyloctadecyl dimethyl ammonium chloride as the microbiocide, together with (2) from about 0.5 to 1.5 weight % of an epoxy-polyoxyalkylene modified organosilicone as a hydrophilic coupling agent, sometimes referred to as a "rewetter" herein, and (3) a tinctorial amount up to about 1% of one or more direct dyes when applied to a suitable non-woven cellulosic-based substrate will produce a colored, waxy, water-insoluble, bioactive, absorbent, wettable finish on the material which retains the dye, bioactive material and the hydrophilic coupling agent yet conforms to the necessary cytotoxicity, non-flammability and anti-static requirements listed above.

While not wishing to be bound by any particular theory it appears that a combination of the three materials produces a type of cross-linked matrix reactively bonded to the fiber of the substrate. The presence of the epoxy-polyoxyalkylene organosilicone material in the treatment bath serves not only to provide the necessary rewetting/absorptive qualities for the finished product but also prevents the silicone quaternary amine bioactive material from complexing and becoming gelled during processing operations thus extending shelf life and reducing the loss of microbiocide from the solution. The aqueous-based solutions used in the process of my invention are typically applied by padding onto a suitable non-woven substrate although other application procedures may be used.

Suitable non-woven substrates are used in the process of my invention are essentially all cellulosic in nature and include paper, cotton, rayon and possibly wool, but not the substrates composed essentially entirely of an acrylic, polyester or nylon fiber. The preferred substrate is a dry laid spray bonded paper toweling material which is bonded with acrylic resins and contains about 80-85% by weight paper (cellulose) with 15-20% by weight acrylic resin binder. This material is available from the Fort Howard Paper Company under their style designation E-43. Also suitable is a wet-laid paper that is creped and print bonded and which is composed of about 90% by weight cellulose and about 10% by weight acrylic binder. Such materials include the Scott Hi-Loft materials under style designations 3051 and 3055 available from the Scott Paper Company. Non-woven substrates containing significantly less than about 80% cellulosic content are not preferred.

The procedure of my invention will now be described with reference to the attached drawing. As shown in the figure a non-woven substrate is directed from a supply reel through a pad bath (the content of which are explained below) and passed through a nip roll to achieve an overall wet pickup (wpu) of between about 75 and 125% calculated on the weight of the non-woven substrate. Preferably the wet pickup is in the range of about 85 to about 115% also expressed on the weight of the substrate. Next the impregnated substrate is passed through a stack of steam cans maintained at a suitable temperature so that dry/cure occurs at between about 280° and 360° F. As the wet material is passed over the series of steam cans the lower stack of cans tends to remove the water and dry the material while the upper stack of cans adds additional heat and cures the material setting the applied components to the substrate. Preferably the material is subjected to a temperature in the range of 280°–300° F. for at least about 5 seconds. The dried, finished product is then led away from the stack of steam cans, rolled and stored wrapped in plastic bags or the like.

The preferred silicone quaternary amine bioactive material is 3-(trimethoxysilyl)-propyloctadecyldimethyl ammonium chloride which is described in U.S. Pat. No. 3,730,701, the disclosure of which is hereby incorporated by reference. A class of suitable bioactive silyl quaternary amine compounds have the formula:

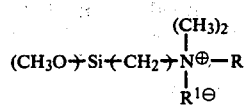

in which R is a $C_{11-22}$ alkyl group and $R^1$ is chlorine or bromine. The preferred silicone quaternary amine is 3-(trimethoxysilyl)-propyloctadecyl dimethyl ammonium chloride and is available as a 42% active solids in methanol from Dow Corning Corporation of Midland, Michigan under the designation DC-5700 (formerly Q9-5700). This material is well accepted in commerce and has been approved not only as a bacteriostatic textile treatment but also as a bactericidal component for medical device/non-drug applications.

As the hydrophilic coupling agent there is used a member of the class of the epoxy-polyoxyalkylene modified organosilicones described in U.S. Pat. No. 4,184,004, the disclosure of which is incorporated herein by reference. The preferred material is available in commerce from Union Carbide Corporation and is believed to respond to the following general structure:

in which the units are end-capping units and are identical to each other, the various "D" and "M" units having the following configuration:

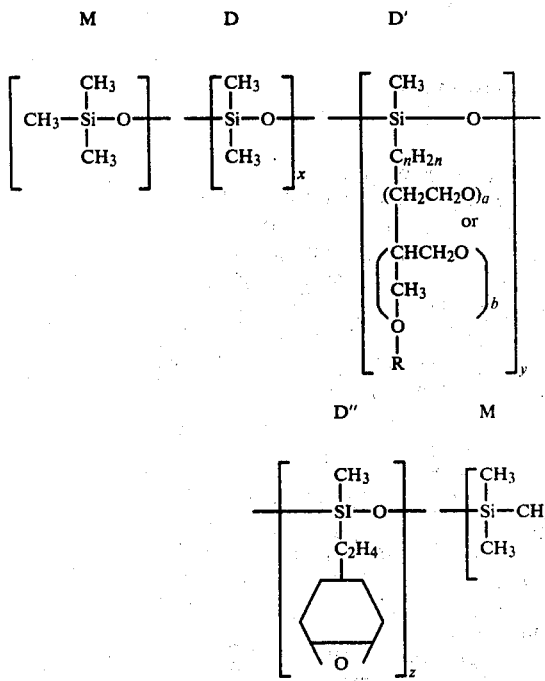

as disclosed in U.S. Pat. No. 4,184,004. In the above formula R represents either hydrogen or methyl and the total of a+b is believed to be from 5 to 200. The average values of x, y and z are as follows:

x = 10 to 50,000;
y = 1 to X;
z = 1 to 0.5x provided that,
y+z ≦ 0.75x
preferably:
x = 25 to 1,000;
y = 1 to 0.5x provided that,
z = 1 to 0.25x and
y+z ≦ 0.5x
most preferably:
x = 50 to 300
y = 1 to 0.25x
x = 1 to 0.15 x, provided that
y+z ≦ 0.25 x
as disclosed at column 3 lines 35-50 of U.S. Pat. No. 4,184,004.

The dyes useful in the process of the present invention are water soluble and are classified as direct cotton dyes or direct dyes, as they dye cotton directly; see Venkataraman, The Chemistry of Synthetic Dyes, Vol. 1 p. 271, Academic Press, Inc., New York, 1952. From this class of dyes one selects a suitable dye, or a group of dyes, that is compatible with the unique bioactive compound/rewetter system used in the process of my invention. The selection is made emperically by testing various candidate dyes. Suitable dyes include:

from Atlantic Color and Chemical:

| Direct Blue NDT | not available |
| --- | --- |
| Direct Blue 2GR-NB | C.I. No. Direct Blue 284 |
| Direct Blue 2RR-NB | C.I. No. Direct Blue 283 |
| Direct Blue 2RL-NB | C.I. No. Direct Blue 286 |
| Direct Blue 3RR-NB | C.I. No. Direct Blue 285 |
| Direct Blue R-NB | not available | from Crompton and Knowles:

| Intralite Blue NB-LL | C.I. Direct Blue 80S |
| --- | --- |
| Intralite Blue FFC | C.I. Direct Blue 71 | from Ciba Geigy:

| Solophenyl Blue BL | C.I. Direct Blue 106 |
| --- | --- |

Additionally included in the pad bath is a minor amount of a binder to assist in retaining the dye on the substrate and to provide a measure of lint control. Suitable binders include polyvinyl alcohol or Rhoplex HA-16 from Rohm and Haas. The amount of binder is adjusted so as not to mask the reactive sites on the substrate nor to compete strongly with the antimicrobial agent for the reactive sites on the substrate.

The manner in which the bioactive compound plus hydrophilic coupling agent are placed onto the substrate may be by brushing, spraying or other suitable means known in the textile arts. I prefer to apply the required components onto the substrate by padding them using a pad bath having generally the following ingredients and amounts expressed in weight percent:

| | range | example |
| --- | --- | --- |
| bioactive compound | 0.2-1.1% | 1.0% |
| epoxy-polyoxyalkylene hydrophilic coupling agent | 0.5-1.5% | 1.0% |
| direct dye | up to 1% | 0.035-0.35 |
| binder | | 1.5-4 |
| alcohol (solvent) | 1-3% | 1.0% |
| water | balance | balance |

As shown in the above table, the amount of the bioactive compound is preferably within the range of about 0.2 to about 1.1% calculated on the weight of the solids present in the pad bath. An amount substantially greater than 1.1% is difficult to retain on the medical substrate without leachability difficulties. The alcohol is used to solubilize the hydrophilic coupling agent which is then added to the bioactive compound to formulate the pad bath.

The pad bath must be applied to the substrate within reasonable temperature limits, for instance room temperature up to about 35° F. otherwise the bath may become unstable and the pad bath itself will react with the sides of its container. Accordingly it is appropriate to prepare the pad bath using cold water and to protect the bath from extreme temperature conditions during storage and operations.

The medical substrate so produced must exhibit an absorptive capacity generally in accordance with ASTM D1117 and demostrate a suitable ability to absorb and retain water.

Additionally bleeding is checked by dipping two pieces of the substrate in water; placing them on either side of a white blotter paper and pressing then observing the blotter paper for possible bleeding. The procedure is repeated using 70% isopropanol or normal saline in place of the water.

Applications for the materials produced by the herein described process include various medical-type substrates such as non-woven bed colored covers and linens, liners and sheets, bandages, dressings, instrument wraps, instrument tray liners, hospital gowns, caps and garments, surgical drapes as well as many other applications.

What is claimed is:

1. A process for making a dyed, absorbent, bioactive wettable medical fabric comprising the steps of:
   (a) mixing (1) a wettable hydrophilic coupling amount of an organosilicone terpolymer of the formula:

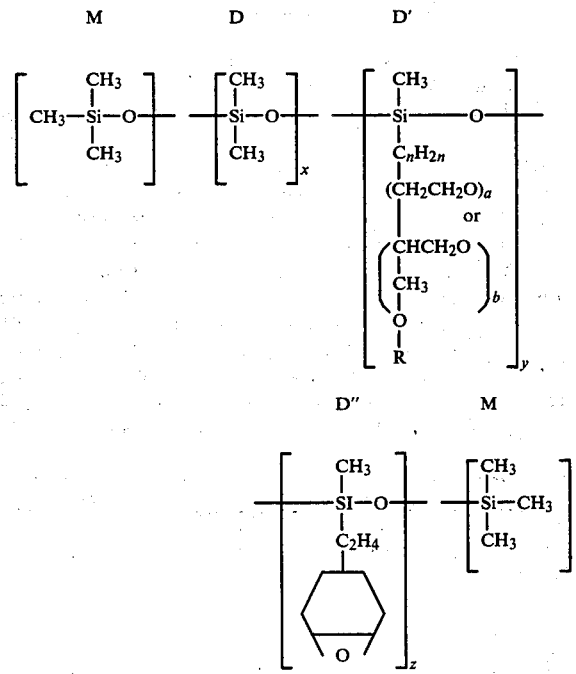

wherein R is hydrogen or methyl, the sum of a+b is in the range of 5 to 200, x is 10 to 50,000, y is 1 to x and z is 1 to 0.5x provided that the sum of y+z is $\leq 0.75x$ with (2) a tinctorial amount of a compatible direct dye, and (3) bioactive amount of a bioactive silyl quaternary amine compounds have the formula:

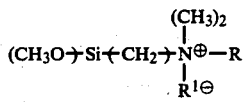

wherein R is an alkyl of 11 to 22 carbon atoms and $R^1$ is a bromine or chlorine; and
   (b) applying the mixture of step (a) to a non-woven cellulose-containing substrate; and
   (c) heating the thus coated substrate from step (b) to dry the substrate and fix the dye, microbiocide and hydrophilic coupling agent to said substrate, thereby producing a dyed, bacteriocidal substantially non-leachable and non-flammable finish which is substantive on said substrate.

2. The process of claim 1 wherein the mixture of step (a) contains from about 0.5 to about 1.5 weight percent of the hydrophilic coupling agent (1), up to 1 weight percent of the direct dye (2), and from about 0.2 to 1.1 weight percent of the bioactive agent (3).

3. The process of claim 1 or 2 wherein step (c) is conducted at a temperature in the range of about 280° F. to about 360° F.

4. The process of claim 1 or 2 wherein said non-woven substrate is composed of at least about 80 weight percent cellulose.

5. The process of claim 4 wherein said non-woven substrate contains from about 80 to 85 weight percent cellulose bonded with about 15 to about 20 weight percent acrylic resin binder.

6. The process of claim 1 or 2 wherein in said hydrophilic coupling agent (1) the sum of a+b is in the range of 5 to 200, x is 50 to 300, y is 1 to 0.25x and z is 1 to 0.5x, provided that the sum of y+z is $\leq 0.25x$; and the microbiocide (3) is 3-(trimethoxysilyl)-propyloctadecyl dimethyl ammonium chloride.

* * * * *

UNITED STATES PATENT AND TRADEMARK OFFICE
Certificate

Patent No. 4,408,996                 Patented October 11, 1983

On petition requesting issuance of a certificate for correction of inventorship pursuant to 35 USC 256, it has been found that the above-identified patent, through error and without any deceptive intent, improperly sets forth the inventorship. Accordingly, it is hereby certified that the correct inventorship of this patent is A. Frank Baldwin, Greensboro, N.C.; Stuart P. Suskind, Valencia, Calif.; Donald M. Patterson, El Paso, Tex.

Signed and Sealed this nineteenth Day of August, 1986.

BRADLEY R. GARRIS,
*Office of the Deputy Assistant
Commissioner for Patents.*